United States Patent
Tavoletti et al.

(10) Patent No.: US 11,819,364 B2
(45) Date of Patent: Nov. 21, 2023

(54) ULTRASOUND PROBE WITH MOVEABLE HEAT SPREADER AND CABLE STRAIN RELIEF

(71) Applicant: KONINKLIJKE PHILIPS N.V., Eindhoven (NL)

(72) Inventors: Steven Michael Tavoletti, Reading, MA (US); John Bench Caswell, Manchester, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 31 days.

(21) Appl. No.: 17/251,985

(22) PCT Filed: Jun. 21, 2019

(86) PCT No.: PCT/EP2019/066562
§ 371 (c)(1),
(2) Date: Dec. 14, 2020

(87) PCT Pub. No.: WO2020/002169
PCT Pub. Date: Jan. 2, 2020

(65) Prior Publication Data
US 2021/0251613 A1      Aug. 19, 2021

Related U.S. Application Data (60) Provisional application No. 62/689,409, filed on Jun. 25, 2018.

(51) Int. Cl.
*A61B 8/00* (2006.01)
*B06B 1/02* (2006.01)
*B06B 1/06* (2006.01)

(52) U.S. Cl.
CPC ............ *A61B 8/546* (2013.01); *A61B 8/4455* (2013.01); *A61B 8/4488* (2013.01);
(Continued)

(58) Field of Classification Search
CPC ..... A61B 8/546; A61B 8/4455; A61B 8/4488; A61B 2562/12; A61B 2562/166; A61B 8/4444; B06B 1/0292; B06B 1/0629
See application file for complete search history.

(56) References Cited

U.S. PATENT DOCUMENTS 4,172,451 A * 10/1979 Kline .................. A61N 1/0587
600/374
4,669,241 A * 6/1987 Kelly ....................... E06B 3/56
52/204.593
(Continued)

FOREIGN PATENT DOCUMENTS

| EP | 2644097 A1 | 10/2013 |
|---|---|---|
| JP | 2017093878 A | 6/2017 |
| WO | 2018019974 A1 | 2/2018 |

OTHER PUBLICATIONS

Berg, Dennis G., "The Basics of Shoulder Screws", Nov. 3, 2011, https://www.machinedesign.com/fastening-joining/article/21834322/the-basics-of-shoulder-screws, Retrieved Oct. 20, 2022 (Year: 2011).*

(Continued)

*Primary Examiner* — Christopher Koharski
*Assistant Examiner* — Taylor Deutsch (57) ABSTRACT

An ultrasound imaging probe includes an ultrasound transducer assembly configured to obtain imaging data associated with a body of a patient; a chassis (304) fixedly secured to the ultrasound transducer assembly; a plurality of heat spreader members (430, 440) positioned around the chassis and configured to provide a thermal path for heat generated by the ultrasound transducer assembly while obtaining the imaging data, wherein the plurality of heat spreader members is movably coupled to the chassis; and a housing (510, 520) positioned around the plurality of heat spreader members, wherein the plurality of heat spreader members is
(Continued)

configured to move relative to the chassis when the housing is positioned around the plurality of heat spreader members.

21 Claims, 6 Drawing Sheets

(52) U.S. Cl.
CPC ..... *A61B 2562/12* (2013.01); *A61B 2562/166* (2013.01); *B06B 1/0292* (2013.01); *B06B 1/0629* (2013.01)

(56) References Cited

U.S. PATENT DOCUMENTS

| | | | |
|---|---|---|---|
| 5,491,451 A * | 2/1996 | English | H03L 7/26 331/3 |
| 5,617,866 A | 4/1997 | Marian, Jr. | |
| 5,810,773 A | 9/1998 | Pesnicak | |
| 6,461,304 B1 * | 10/2002 | Tanaka | A61B 8/12 600/462 |
| 2007/0142970 A1 * | 6/2007 | Burbank | A61B 34/70 700/251 |
| 2011/0059669 A1 | 3/2011 | He et al. | |
| 2012/0245470 A1 | 9/2012 | Ooishi et al. | |
| 2014/0364742 A1 | 12/2014 | Cho et al. | |
| 2015/0173169 A1 * | 6/2015 | Zhang | H01L 23/3675 361/720 |
| 2017/0188995 A1 | 7/2017 | Bruestle et al. | |

OTHER PUBLICATIONS

PCT/EP2019/066562 ISR & WO, Oct. 14, 2019, 17 Page Document.

* cited by examiner

ULTRASOUND PROBE WITH MOVEABLE HEAT SPREADER AND CABLE STRAIN RELIEF

CROSS-REFERENCE TO PRIOR APPLICATIONS

This application is the U.S. National Phase application under 35 U.S.C. § 371 of International Application No. PCT/EP2019/066562, filed on Jun. 21, 2019, which claims the benefit of U.S. Provisional Patent Application No. 62/689,409, filed on Jun. 25, 2018. These applications are hereby incorporated by reference herein.

TECHNICAL FIELD

The present disclosure relates generally to an ultrasound imaging probe, and in particular, to an ultrasound imaging probe with heat spreader members that can move relative to a chassis and/or a cable strain relief during assembly with external housing.

BACKGROUND

External ultrasound imaging probes have become indispensable diagnostic tools in modern day medical care due to their non-invasive nature and ever increasing resolution. In a conventional ultrasound imaging probe, an acoustic stack and printed circuit boards are fixedly secured to an internal frame, which is fixedly secured to a heat spreader and an external housing. All these components have to fit with one another with tight tolerances in order to achieve a high quality ultrasound imaging probe with an exterior surface that is free of gaps. Gaps, if present, not only are unsightly to customers but also can trap contaminants. What can make things worse is the variation or inconsistency between gaps on a single device or across different devices. While gaps are undesirable, it can be costly and challenging to rid conventional ultrasound imaging probes of them.

SUMMARY

Embodiments of the present application provide a substantially gapless ultrasound imaging probe with large manufacturing tolerance. An exemplary ultrasound probe according to the present disclosure includes a housing, a chassis, an ultrasound transducer assembly fixedly secured to the chassis, a plurality of heat spreader members positioned around the chassis, and a cable strain relief. The plurality of heat spreader members is movably coupled to the chassis and the cable strain relief. The movable coupling allows the plurality of heat spreader members to move in more than one dimension with respect to the cable strain relief and/or the chassis while a portion of the cable strain relief, the plurality of heat spreader members and the chassis are being enclosed by the housing. Advantageously, the movable coupling allows for manufacture of high quality external ultrasound probes that have only small exterior seams that have consistent width within a single device and across different devices. A filling material, such as room-temperature-vulcanizing (RTV) rubber, can be positioned in the space between the housing members and/or the heat spread members.

According to an exemplary embodiment, an ultrasound imaging probe is provided. The probe includes an ultrasound transducer assembly configured to obtain imaging data associated with a body of a patient; a chassis fixedly secured to the ultrasound transducer assembly; a plurality of heat spreader members positioned around the chassis and configured to provide a thermal path for heat generated by the ultrasound transducer assembly while obtaining the imaging data, wherein the plurality of heat spreader members is movably coupled to the chassis; and a housing positioned around the plurality of heat spreader members, wherein the plurality of heat spreader members is configured to move relative to the chassis when the housing is positioned around the plurality of heat spreader members.

In some embodiments, the probe further includes a retention clip positioned around proximal ends of the plurality of heat spreader members. In some embodiments, the housing comprises a nosepiece sized and shaped to receive the ultrasound transducer assembly. In some embodiments, the plurality of heat spreader members is movably coupled to the chassis by two shoulder screws and the plurality of heat spreader members is configured to move in more than one dimension relative to the chassis. In some embodiments, the ultrasound transducer assembly comprises: a lens; a transducer array; and a backing block. In some embodiments, the probe further includes a plurality of printed circuit boards to the chassis, wherein the plurality of printed circuit boards are in communication with the ultrasound transducer assembly. In some embodiments, the probe further includes a filling material disposed between the housing and the plurality of heat spreader members. In some embodiments, the filling material is formed of a room-temperature-vulcanizing rubber. In some embodiments, the probe further includes a cable strain relief movably coupled to the plurality of heat spreader members, wherein the plurality of heat spreader members is configured to move in more than one dimension relative to the cable strain relief. In some embodiments, the probe further includes an elastic ring member, wherein the cable strain relief comprises a distal lip adjacent a distal end of the cable strain relief and a proximal lip proximal to the distal lip, wherein the distal lip of the cable strain relief is sized and shaped to engage a shoulder defined at proximal portions of the plurality of heat spreader members, and wherein when the distal lip engages the shoulder, the elastic ring member is disposed between the proximal lip and proximal ends of the plurality of heat spreader members. In some embodiments, the elastic ring member is formed of a thermally conductive elastomer. In some embodiments, the probe further includes a thermally-conductive gap pad disposed between the chassis and at least one of the plurality of heat spreader members.

According to an exemplary embodiment, a method of manufacturing an ultrasound imaging probe is provided. The method includes obtaining an ultrasound transducer assembly fixedly secured to a chassis; movably coupling the chassis to a plurality of heat spreader members; and enclosing the plurality of heat spreader members, the chassis and the ultrasound transducer assembly in a housing while moving the plurality of heat spreader members relative to the chassis.

In some embodiments, movably coupling the chassis to the plurality of heat spreader members comprises coupling the chassis to the plurality of heat spreader members by two shoulder screws. In some embodiments, the method further includes coupling a thermally-conductive gap pad to the chassis and/or at least one of the plurality of heat spreader members, such that the thermally-conductive gap pad is positioned between the chassis and the at least one of the plurality of heat spreader members. In some embodiments, moving the plurality of heat spreader members relative to the chassis comprises moving the plurality of heat spreader members about the two shoulder screws in more than one dimension. In some embodiments, the method further includes movably coupling a cable strain relief to proximal ends of the plurality of heat spreader members. In some embodiments, movably coupling the cable strain relief to the proximal ends of the plurality of heat spreader members comprises coupling the cable strain relief to the proximal ends of the two heat spreader halves with an elastic ring member. In some embodiments, enclosing the plurality of heat spreader members, the chassis and the ultrasound transducer assembly in the housing comprises moving the plurality of heat spreader members relative to the cable strain relief. In some embodiments, moving the plurality of heat spreader members relative to the cable strain relief comprises pivoting the plurality of heat spreader members relative to the cable strain relief.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
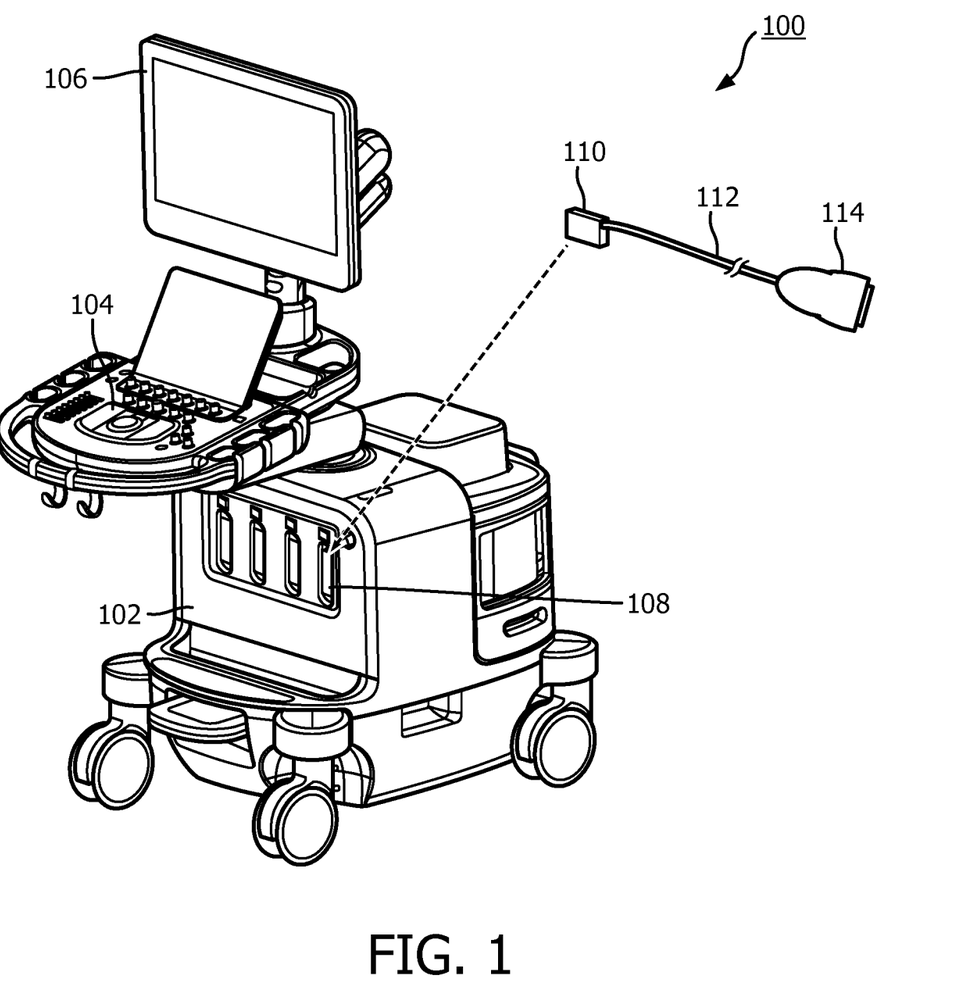
FIG. 1 is a diagrammatic perspective view of an ultrasound imaging system including an ultrasound imaging probe, according to aspects of the present disclosure.

FIG. 1 is a diagrammatic perspective view of an ultrasound imaging system 100, according to aspects of the present disclosure. Ultrasound imaging system 100 includes a console 102 and an ultrasound imaging probe 114. The ultrasound imaging probe 114 is connected to a cable 112 that is coupled to a connector 110. The ultrasound imaging probe 114 can be brought into communication with the console 102 by connecting the connector 110 to a connector receptacle 108 on the console 102. The console 102 includes a control interface 104 and a display device 106. In embodiments represented in FIG. 1, the console 102 can include a plurality of wheels such that the console 102 can roll around on the floor.

The ultrasound imaging probe 114 can be sized and shaped, structurally arranged, and/or otherwise configured for handheld use by a user. During use, the ultrasound imaging probe 114 can be placed on or near the anatomy of a subject to obtain imaging data. In some instances, the subject can be a patient. In some other instances, the subject can be an animal other than a human being. The ultrasound imaging probe 114 may be placed directly on the body of the subject and/or adjacent the body of the subject. For example, the ultrasound imaging probe 114 may be put in contact with the body of the subject while obtaining imaging data. In some embodiments, the ultrasound imaging probe 114 can include an ultrasound transducer array of a plurality of ultrasound transducer elements configured to obtain imaging data of the patient anatomy.

Electrical signals representative of the imaging data can be transmitted from the ultrasound imaging probe 114 to the connector 110 along electrical conductors of the cable 112. With the connector 110 coupled to the connector receptacle 108 on the console 102, the electrical signals can be transmitted to the console 102. The console 102 includes one or more processors that can process the electrical signals and output a graphical representation of the imaging data to the display device 106. A sonographer can control imaging data acquisition of the ultrasound imaging probe 114 via the control interface 104 of the console 102. In some implementations, the connector 110 includes one or more male or female zero insertion force (ZIF) connectors, one or more low insertion force (LIF) connectors, flat flexible connectors (FFCs), ribbon cable connectors, and serial advanced technology attachment (SATA) connectors. In the some embodiments, instead of the console 102, the ultrasound imaging system 100 can include a mobile device, such as a tablet computer, a smart phone, a laptop, or a personal data assistant (PDA). For example, in an embodiment where a tablet computer is used instead of the console 102, the touch screen serves as the control interface and the display device. In these embodiments, the connector 110 can be a Universal Serial Bus (USB) connector of any version or a mini USB of any version.

Figure 2:
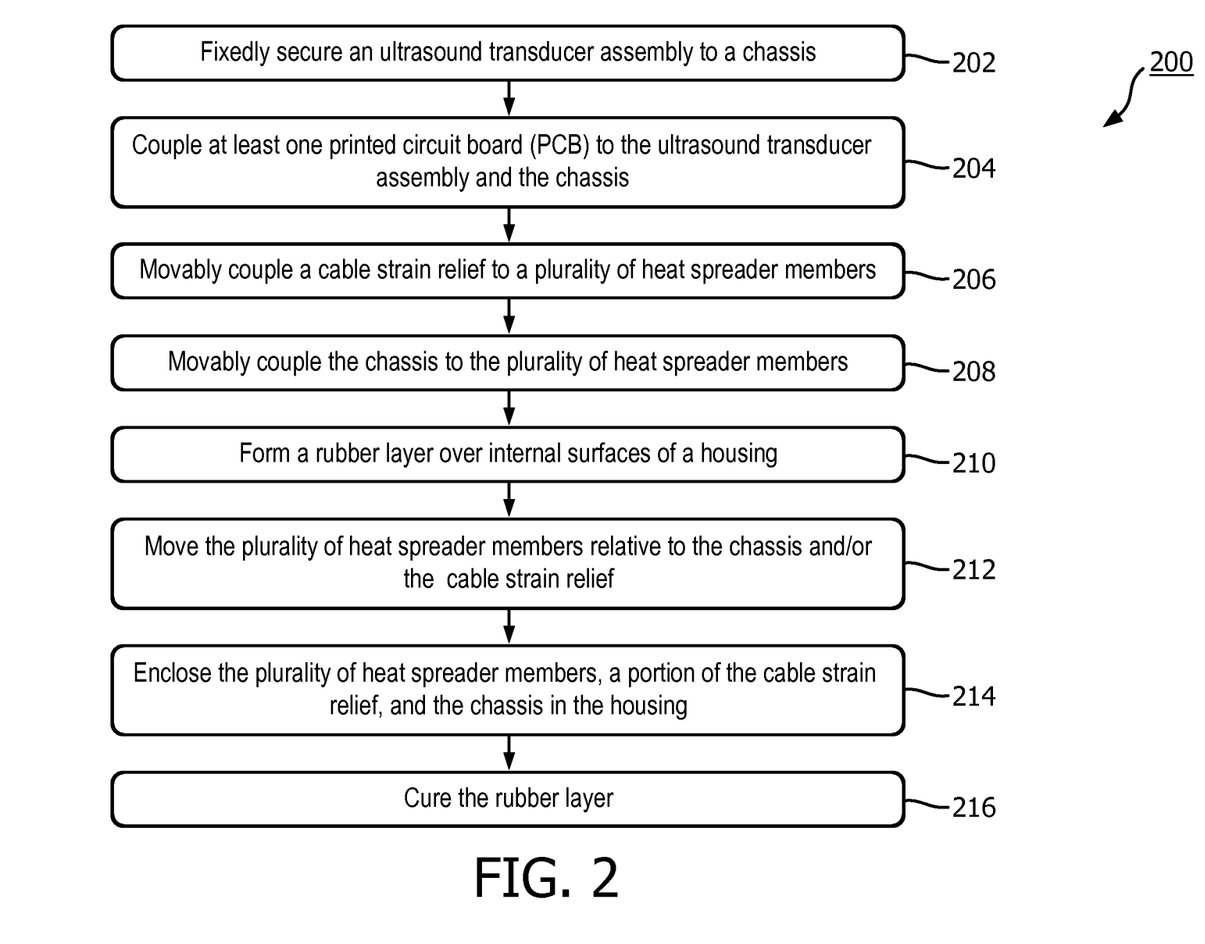
FIG. 2 illustrates a flow chart of a method of manufacturing an ultrasound imaging probe, according to aspects of the present disclosure.

Referring now to FIG. 2, illustrated therein is a flowchart of a method 200 of manufacturing an ultrasound imaging probe, such as the ultrasound imaging probe 114 in FIG. 1. The method 200, as discussed below, can manufacture a substantially gapless ultrasound imaging probe without having to adopt tight engineering tolerances. The method 200 is merely an example, and is not intended to limit the present disclosure beyond what is explicitly recited in the claims. Additional operation can be provided before, during, and after the method 200, and some operations can be replaced, eliminated, or moved around for additional embodiments of the method 200. The method 200 will be described in conjunction with FIGS. 3, 4, 5, and 6.

Figure 3:
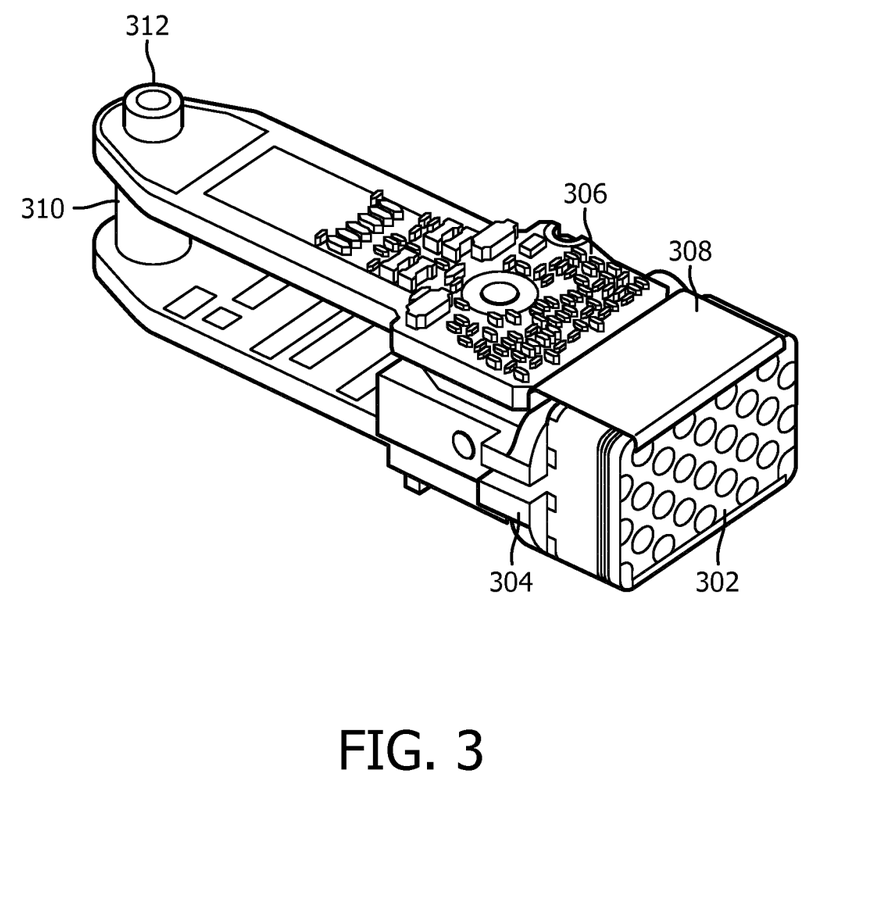
FIG. 3 is a diagrammatic perspective view of an ultrasound imaging probe, according to aspects of the present disclosure.

The method 200 begins at block 202 where an ultrasound transducer assembly 302 is fixedly secured to a chassis 304 (FIG. 3). In some embodiments, the ultrasound transducer assembly 302, which can also be referred to as the ultrasound transducer stack 302, can include a lens, an ultrasound transducer array, and an acoustic backing block.

The ultrasound transducer assembly 302 can include one or more acoustic elements. For example, a plurality of acoustic elements can be arranged in an array. For example, an ultrasound transducer array can include any suitable number of individual acoustic elements between 2 acoustic elements and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. The ultrasound transducer assembly 302 can include suitable configuration, such as a planar array, a linear array, a phased array, a curved array, etc. For example, the ultrasound transducer assembly 302 can include a one-dimensional array, 1.x-dimensional array, such as a 1.5-dimensional array, or a two-dimensional array, in some instances. In that regard, the ultrasound transducer assembly 302 can be configured obtain one-dimensional, two-dimensional, and/or three-dimensional images of the anatomy of the patient. The ultrasound transducer assembly 302 can include a matrix array, including one or more segments of ultrasound elements (e.g., one or more rows, one or more columns, and/or one or more orientations) that can be uniformly or independently controlled and activated. The ultrasound transducer assembly 302 can include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof.

The lens of the ultrasound transducer assembly 302 can have an acoustic impedance configured to facilitate transmission of ultrasound energy from the array into the patient's anatomy. The backing block of the ultrasound transducer assembly 302 is used to attenuate or absorb acoustic energy not directed to the anatomy of interest. The backing block may be disposed adjacent to and/or in contact with the ultrasound transducer array. The backing block can be formed of any suitable material, such as polymers, graphite, composites, ceramics, metals, or any combination thereof.

In some implementations, the ultrasound transducer assembly 302 is fixedly secured to the chassis 304 by mechanical fixtures and/or adhesive. For example, a proximal surface of the ultrasound transducer assembly 302 can have one or more projections that can be received within one or more grooves on a distal surface of the chassis 304. In the embodiments represented in FIG. 3, the ultrasound transducer array of the ultrasound transducer assembly 302 is electrically coupled to one or more flexible circuits 308 that extend proximally along the chassis 304.

The method 200 proceeds to block 204 (FIG. 2) where at least one printed circuit board (PCB) 306 is coupled to the ultrasound transducer assembly 302 and the chassis 304 (FIG. 3). In some embodiments, the at least one PCB 306 includes a plurality of electrical contacts that are configured to engage a plurality of electrical contacts on the one or more flexible circuits 308. By electrically connecting the at least one PCB 306 to the one or more flexible circuits 308 coupled to the ultrasound transducer assembly 302, the at least one PCB 306 can be electrically coupled to and/or in communication with the ultrasound transducer array in the ultrasound transducer assembly 302. In some implementations, the at least one PCB 306 can be fixedly secured to the chassis 304 by a fastener or a screw. In embodiments represented in FIG. 3, the at least one PCB 306 includes two PCBs 306 that are both mechanically coupled to the chassis 304 by a screw and pressed on a portion of the flexible circuit 308. In these embodiments, proximal portions of the two PCBs 306 are secured to a spacer tube 310 by at least one screw 312. The spacer tube 310 maintains spacing between the two PCBs 306.

Figure 4:
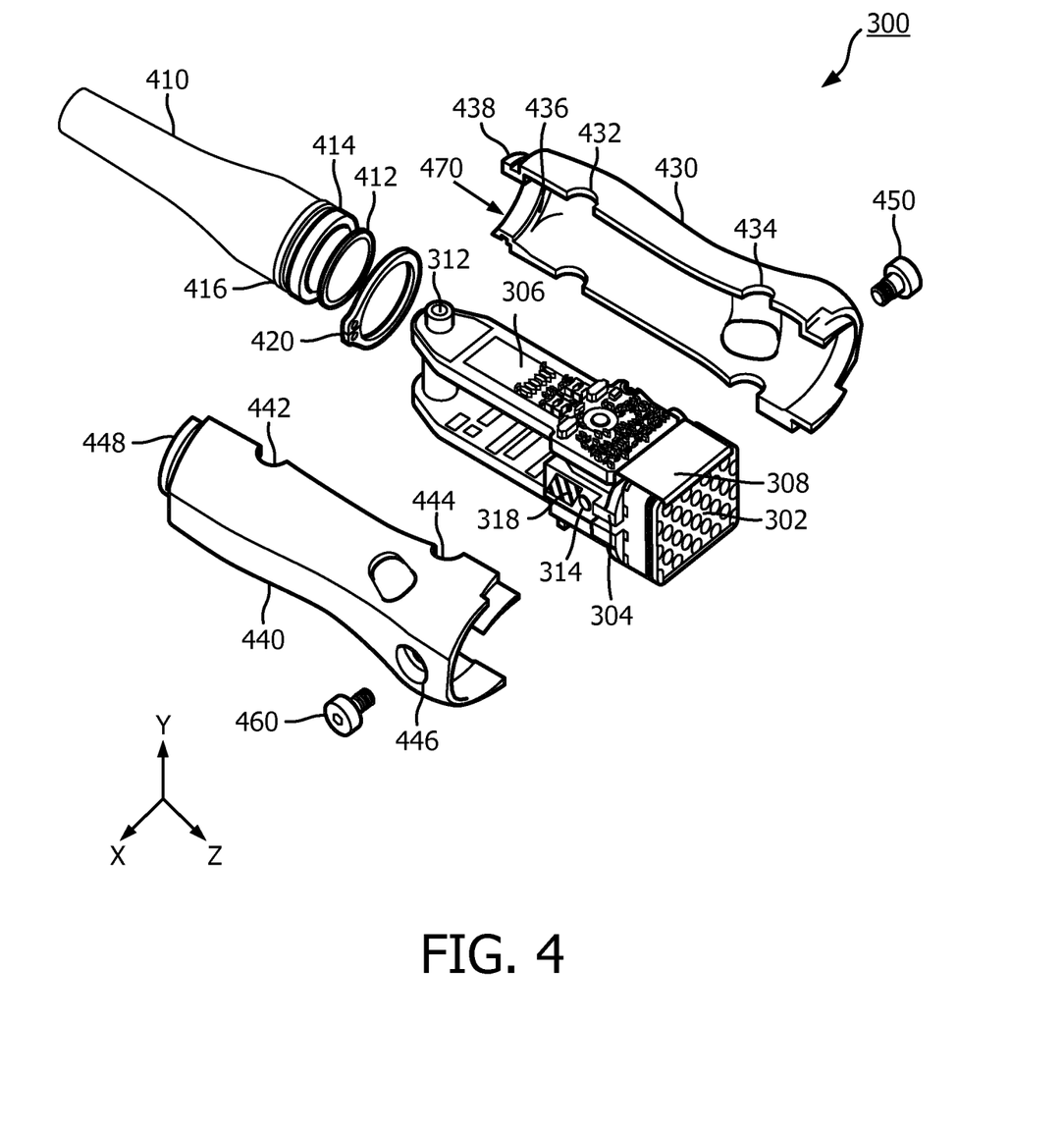
FIG. 4 is a diagrammatic perspective view of an ultrasound imaging probe and fixtures coupling heat spreader members to a cable strain relief and a chassis, according to aspects of the present disclosure.

The method 200 proceeds to block 206 (FIG. 2) where a cable strain relief 410 is movably coupled to a plurality of heat spreader members (FIG. 4). The cable strain relief 410 reduces strain exerted on a cable that includes electrical conductors in electrical communication with the PCBs 306. In some embodiments, the cable strain relief 410 includes a distal lip 412 at a distal end of the cable strain relief 410 and a proximal lip 416 proximal to the distal lip 412. In the embodiments represented in FIG. 4, the cable strain relief 410 is cylindrical in shape and each of the distal lip 412 and the proximal lip 416 is annular in shape. In some embodiments represented in FIG. 4, the plurality of heat spreader members include two heat spreader members 430 and 440. In some other embodiments, the plurality of heat spreader members can include three, four, or more heat spreader members. The heat spreader members 430 and 440 are configured to provide a thermal path for heat generated by the ultrasound transducer assembly 302. The plurality of heat spreader members can be made of thermally conductive materials, such as silver, copper, gold, aluminum, iron, zinc, alloys, graphite, and/or combinations thereof. In the embodiments represented in FIG. 4, each of heat spreader members 430 and 440 includes a shoulder, such as the shoulder 436. In some implementations, a cable with a plurality of electrical conductors, such as the cable 112 in FIG. 1, can extend distally through a lumen within the cable strain relief 410 such that the plurality of electrical conductors can be electrically coupled to the PCBs 306. For the ease of manufacturing, the plurality of electrical conductors of the cable is electrically coupled to the PCBs 306 before the cable strain relief 410 is movably coupled to the plurality of heat spreader members 430 and 440.

In some implementations, the cable strain relief 410 is movably coupled to the plurality of heat spreader members 430 and 440 by a retention clip 420. The heat spreader members 430 and 440 can include a semi-annular groove 438 and 448, respectively. The semi-annular grooves 438 and 448 are configured to form an annular groove when the heat spreader members 430 and 440 are positioned adjacent, near, and/or in contact with one another. The retention clip 420 can be switched between an open configuration with a first inner diameter and a closed configuration with a second inner diameter smaller than the first diameter (the closed configuration shown in FIG. 4). To couple the cable strain relief 410 to the heat spreader members 430 and 440, the cable strain relief 410 is moved into the space between the heat spreader members 430, 440. The distal lip 412 can be an area of increased diameter that is positioned distally past the shoulder 436. Accordingly, when the heat spreader members 430, 440 are closed around the cable strain relief 410, the proximal portion of the distal lip 412 can contact the shoulder 436 such that the shoulder 436 limits proximal movement of the cable strain relief 410 relative to the heat spreader members 430, 440. The proximal lip 416 can be an area of increased diameter that is positioned proximal of the proximal end of the heat spreader members 430, 440. Accordingly, when the heat spreader members 430, 440 are closed around the cable strain relief 410, the proximal lip 416 limits distal movement of the cable strain relief 410 relative to the heat spreader members 430, 440. The retention clip 420, which goes around the semi-annular grooves 438 and 448 in the open configuration, can be closed to engage the semi-annular grooves 438 and 448, thereby bringing the heat spreader members 430 and 440 toward one another. When received in the annular groove and in the closed position, the retention clip 420 can limit the relative movement between the heat spreader member 430 and the heat spreader member 440. The retention clip 420 does not eliminate movement entirely, such as occurs when fixedly securing the components. That is, while coupling components such as the retention clip 420 are used to limit movement of the components, the heat spreader members 430, 440 and the cable strain relief 410 are moveable relative to one another while the retention clip 420 is in place. Also, when the closed retention clip 420 engages the annular groove, the shoulders of the heat spreader members 430 and 440 can limit the translational movement of the cable strain relief 410 relative to the heat spreader members 430 and 440 to a difference between a distance separating the distal lip 412 and the proximal lip 416 and a distance separating the shoulders and a proximal surface 470 of the heat spreader members 430 and 440. The relative movement between components can be referred as a play herein. The play can be damped by an elastic ring member 414. In some embodiments, the elastic ring member 414 can be formed of a thermally and/or electrically conductive elastomer, such as an elastomer including a binder and thermally and/or electrically conductive filler particles. Examples of the binder include silicone, fluorosilicone, ethylene propylene diene monomer (EPDM) rubber, fluorocarbon-fluorosilicone, or a combination thereof. Examples of the filler particles include pure silver particles, silver-plated copper particles, silver-plated aluminum particles, silver-plated nickel particles, silver-plated glass particles, nickel-plated graphite particles, nickel-plated aluminum particles, unplated graphite particles, or combinations thereof. The retention clip 420 and the elastic ring member 414 provide flexibility to the coupling between the cable strain relief 410 and the heat spreader members 430 and 440.

In some embodiments, the retention clip 420, when closed to engage the annular groove, does not rigidly press the heat spreader members 430 and 440 together. In those embodiments, the heat spreader members 430 and 440 can move relative to the cable strain relief 410 in more than one dimension (e.g., in the X, Y, and/or Z dimensions) without decoupling from the cable strain relief 410. For example, when the cable strain relief 410 is fixed in position, a distal portion of the heat spreader members 430 and 440 can pivot along the Y-Z plane or along the X-Z plane. Relative to the cable strain relief 410, the heat spreader members 430 and 440 can be configured for any suitable movement including rotation, pivoting, translation radially (inward/outward), translation longitudinally (proximally/distally), and/or combinations thereof.

The method 200 proceeds to block 208 (FIG. 2) where the chassis 304 is movably coupled to the heat spreader members 430 and 440 (FIG. 4). In some embodiments, each of the heat spreader members 430 and 440 is coupled to the chassis 304 by a fixture that allows the heat spreader members 430 and 440 to move relative to the chassis 304. In some implementations, the heat spreader members 430 and 440 are coupled to the chassis 304 by a shoulder screw 450 and a shoulder screw 460, respectively. For example, the shoulder screw 460 can extend through a screw hole 446 on the heat spreader member 440 and thread into the chassis 304 at the hole 314. Similarly, the shoulder screw 450 can extend through a screw hole on the heat spreader member 430 and thread into the chassis 304. Each of the shoulder screws 450 and 460 includes an unthreaded section adjacent to the screw head and a threaded section away from the screw head. In some embodiments, when the threaded sections of the shoulder screws 450 and 460 are threaded into the chassis 304, the unthreaded sections that interface the heat spreader members 430 and 440 can allow the heat spreader members 430 and 440 to move relative to the chassis 304. For example, the heat spreader members 430, 440 can translate or pivot along the Y-Z plane with respect to an axis between the shoulder screws 450 and 460. That is, when the ultrasound transducer assembly 302 is fixed in position, the heat spreader members 430 and 440 can pivot along the Y-Z plane with respect to the shoulder screws 450 and 460. Movably coupling the heat spreader members 430, 440 to the chassis 304 using the shoulder screws 450, 460 allows the heat spreader members 430 and 440 to move relative to the chassis 304 in more than one dimension (e.g., in the X, Y, and/or Z dimensions) without decoupling from the chassis 304. Relative to the chassis 304, the heat spreader members 430 and 440 can be configured for any suitable movement including rotation, pivoting, translation radially (inward/outward), translation longitudinally (proximally/distally), and/or combinations thereof.

In some implementations, because the shoulder screws 450 and 460 are made of thermally and/or electrically conductive materials, such as steel, silver, copper, gold, aluminum, iron, zinc, or an alloy thereof, the shoulder screws 450 and 460 create heat paths from the chassis 304 to the heat spreader members 430 and 440. In some embodiments, to further improve the thermal conduction between the chassis 304 and the heat spreader members 430 and 440, a plurality of gap pads, such as a gap pad 318 in FIG. 4, can be positioned between surfaces of the chassis 304 and surfaces of the heat spreader members 430 and 440. The gap pad 318 can be in direct contact with the chassis 304 and with the heat spreader members 430 and 440, even if the chassis 304 and the heat spreader members 430 and 440 do not directly contact one another. The gap pad 318 can be coupled (e.g., thermally conductive adhesive, mechanical attachment, etc.) to the chassis 304 and/or the heat spreader members 430 and 440 such that a thermal path extends between the chassis 304 to the heat spreader members 430, 440 via the gap pad 318. In some instances, the gap pad 318 can be formed of an elastomer including a binder and thermally and/or electrically conductive filler particles. Examples of the binder include silicone, fluorosilicone, ethylene propylene diene monomer (EPDM) rubber, fluorocarbon-fluorosilicone, or a combination thereof. Examples of the filler particles include pure silver particles, silver-plated copper particles, silver-plated aluminum particles, silver-plated nickel particles, silver-plated glass particles, nickel-plated graphite particles, nickel-plated aluminum particles, unplated graphite particles, or combinations thereof. In some implementations, the elastomer can be applied to surfaces of the chassis 304 because the elastomer is cured and before the heat spreader members 430 and 440 are coupled to the chassis 304 by the shoulder screws 450 and 460.

In some embodiment, the heat spreader members 430 and 440 are sized and shaped to enclose the ultrasound transducer assembly 302, the chassis 304, and the PCBs 306. In those embodiments, the heat spreader members 430 and 440 include a plurality of cutoffs to accommodate or allow access to features of the ultrasound transducer assembly 302, the chassis 304, and the PCBs 306. For example, a cutoff 432 on the heat spreader member 430 and a cutoff 442 on the heat spreader member 440 can form an opening that provides access to the screw 312. For another example, a cutoff 434 on the heat spreader member 430 and a cutoff 444 on the heat spreader member 440 can form an opening that provides access to a screw that secures the PCB 306 to the chassis 304.

It is noted that operations in blocks 206 and 208 can be performed sequentially or simultaneously. In some embodiments, operations in block 208 can be performed before operations in block 206.

Figure 5:
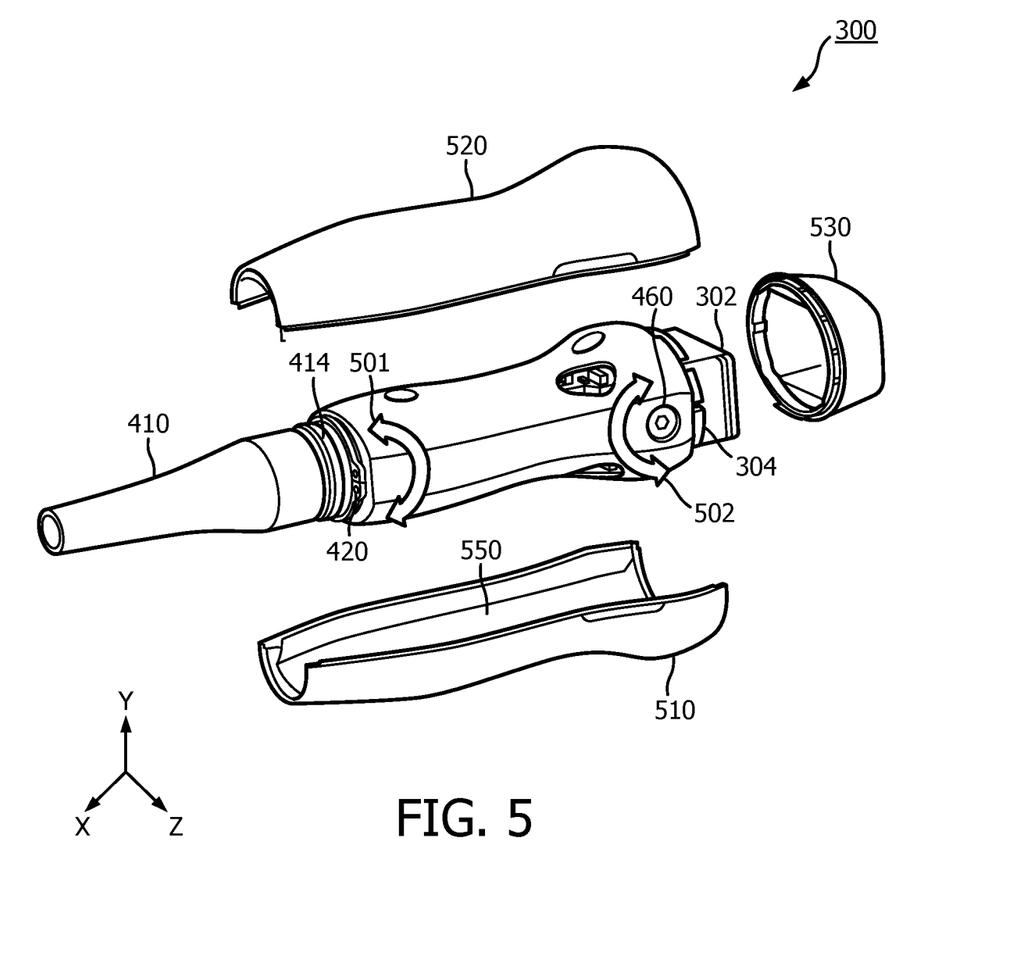
FIG. 5 is a diagrammatic perspective view of an ultrasound imaging probe being enclosed by members of a housing, according to aspects of the present disclosure.

The method 200 then proceeds to block 210 (FIG. 2) where a filling material 550 is positioned over internal surfaces of the housing, such as the housing member 510 and the housing member 520 (FIG. 5). In some embodiments, the filling material 550 can include a room-temperature-vulcanizing (RTV) rubber or silicone rubber. The filing material 550 can be an elastic material. While rubber is mentioned, any suitable adhesive material, such as epoxy, can be used. Before the rubber/epoxy that forms the filling material 550 is cured at block 216, to be described further below, the filling material can be flowable and applied or coated on the internal surfaces of the housing, e.g., by use of an applicator.

As described further herein, the operations in blocks 212 and 214 can be performed sequentially or simultaneously. In some embodiments, operations in block 214 can be performed before operations in block 212.

The method 200 proceeds to block 212 (FIG. 2) where the heat spreader members 430 and 440 are moved relative to the chassis 304 and/or the cable strain relief 410 (FIG. 5). For example, the movement can occur as a result of block 214. As shown by a curved arrow 501, the heat spreader members 430 and 440 can be moved relative to the cable strain relief 410. Additionally, as shown by a curved arrow 502, the heat spreader members 430 and 440 can be moved relative to the chassis 304, e.g., around the shoulder screws 450 and 460. That means, the chassis 304, the heat spreader members 430 and 440, and the cable strain relief 410 act as three segments interlinked by movable coupling, with the chassis 304 being a distal segment, the heat spreader members 430 and 440 being the middle segment, and the cable strain relief 410 being a proximal segment. Because the heat spreader members 430 and 440 (i.e. the middle segment) are movably coupled to and sandwiched between the chassis 304 (i.e. the distal segment) and the cable strain relief 410 (i.e. the proximal segment), the heat spreader members 430 and 440 can be said to be floating. In some embodiments of the present disclosure, when the chassis 304, the heat spreader members 430 and 440, and the cable strain relief 410 are to be enclosed in a housing that includes a housing member 510, a housing member 520, and a nosepiece 530, the three segments can be moved/pivoted relative to one another to compensate for dimensional variations in the housing member 510, the housing member 520, the nosepiece 530, the chassis 304, the heat spreader members 430 and 440, and the cable strain relief 410.

The method 200 then proceeds to block 214 (FIG. 2) where the plurality of heat spreader members 430 and 440, a portion of the cable strain relief 410, and the chassis 304 are enclosed in the housing 510, 520 (FIG. 5). The enclosing can cause movement described with respect to block 212. With the filling material 550 applied to the internal surfaces of the housing and the three segments moved to adapt to the dimensions of the housing, the housing members 510 and 520 can be pressed against the heat spreader members 430 and 440 without being strained. This is so because the housing members 510 and 520 are not pressed onto a rigid structure but a movable one. The engineering variations (e.g., tolerances) can be absorbed and eliminated by the movable coupling between the heat spreader members 430 and 440 and the cable strain relief 410 as well as between the heat spreader members 430 and 440 and the chassis 304. The filling material 550 flows into and fills recesses within the interior space between the housing members 510, 520 and/or the heat spreader members 430, 440. In some embodiments, the housing members 510 and 520 can cover all access openings or screw holes of the heat spreader members 430 and 440. In some implementations, the housing members 510 and 520 can also cover the retention clip 420 and the elastic ring member 414. In some embodiments represented in FIG. 5, the nosepiece 530 of the housing can be secured to the housing members 510 and 520 by mechanical fixtures or adhesive. In some other embodiments, besides being secured to the housing members 510 and 520, the nosepiece 530 can also be secured to the chassis 304 by mechanical fixtures or adhesive. The nosepiece 530 includes an opening that tracks the shape of the ultrasound transducer assembly 302. When secured to the housing members 510 and 520 and/or the chassis 304 and after the filling/rubber material 550 has cured, the nosepiece 530 can prevent the ultrasound transducer assembly 302 from moving or pivoting relative to the heat spreader members 430 and 440. Similarly, when the housing members 510 and 520 are pressed onto and enclose the heat spreader members 430 and 440, and the filling/rubber material 550 has cured, the cable strain relief 410 is prevented from movement/pivoting relative to the heat spreader members 430 and 440. In some embodiments, when enclosed in the housing and after the filling/rubber material 550 has cured, the pliable three segments no longer move relative to one another.

It is noted that the operations in blocks 212 and 214 can be performed simultaneously or in an alternating fashion. For example, the heat spreader members 430 and 440 can be moved relative to the cable strain relief 410 and/or the chassis 304 while the housing members 510 and 520, whose internal surfaces are coated with the filling/rubber material 550, are being pressed onto the heat spreader members 430 and 440. For another example, after the housing members 510 and 520 enclose the heat spreader members 430 and 440 and a portion of the cable strain relief 410, the chassis 304 can be moved relatively to the heat spreader members 430 and 440 around the shoulder screws 450 and 460 to be received within the nosepiece 530.

Figure 6:
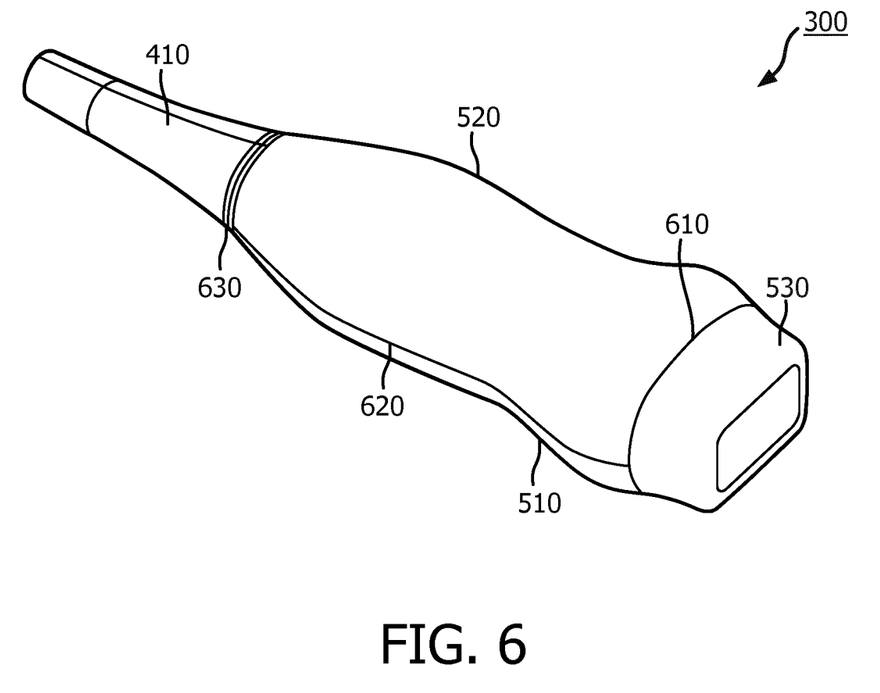
FIG. 6 is a diagrammatic perspective view of a fully assembled ultrasound imaging probe, according to aspects of the present disclosure.

The method 200 proceeds to block 216 (FIG. 2) where the filling/rubber material 550 is cured (FIG. 6). When the housing members 510 and 520 that are coated with the filling/rubber material 550 are pressed onto the heat spreader members 430 and 440 for enclosure, excess filling/rubber material 550 can be squeezed out from gaps and seems of the housing members 510 and 520. The excess or overflow of filling/rubber material 550 is then removed from the housing. In some embodiments, the filling/rubber material 550 can be cured at room temperature (20° C.-25° C.) for three (3) to five (5) days, depending on the amount, thickness, and/or other properties of the filling/rubber material. In some other embodiments, to accelerate the curing process, the ultrasound imaging probe 300 can be placed in a climate controlled chamber or oven for elevated or decreased temperature and/or humidity. For example, the ultrasound imaging probe 300 can be placed in an oven set at 50° C. and 50% relative humidity for one (1) day to cure the filling/rubber material 550.

Referring still to FIG. 6, shown therein is the ultrasound imaging probe 300 manufactured using the method 200 in FIG. 2. The ultrasound imaging probe 300 includes a seam 610 between the nosepiece 530 and the housing members 510 and 520, a seam 620 between the housing members 510 and 520, and a seam 630 between the cable strain relief 410 and the housing members 510 and 520. Because the heat spreader members 430 and 440 are floating between the cable strain relief 410 and the chassis 304, the seams 610, 620 and 630 are minimized or can be controlled at a consistent levels. For the same reason, the ultrasound imaging probe 300 is substantially free of gaps, not to be mention gaps of varying sizes.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging probe, comprising:
    an ultrasound transducer assembly configured to obtain imaging data associated with a body of a patient;
    a chassis fixedly secured to the ultrasound transducer assembly;
    a plurality of heat spreader members configured to provide a thermal path for heat generated by the ultrasound transducer assembly while obtaining the imaging data;
    a plurality of fasteners coupling the plurality of heat spreader members and the chassis, wherein each of the plurality of fasteners comprises:
        a first portion comprising a first shape fixedly secured to the chassis; and
        a second portion opposite to the first portion and configured to interface with a respective heat spreader member, wherein the second portion comprises a different, second shape;
    a housing positioned around the plurality of heat spreader members, wherein the housing defines an interior space, wherein the plurality of heat spreader members and the chassis are positioned within the interior space; and
    a filling material positioned within the interior space, wherein the filling material comprises an uncured state and a cured state,
    wherein, in the uncured state, the filling material and the second portion of each of the plurality of fasteners are configured to allow movement of the plurality of heat spreader members such that a positioning of the plurality of heat spreader members within the interior space is adaptable to dimensions of the interior space, and
    wherein, in the cured state, the filling material is configured to prevent the movement of the plurality of heat spreader members.

2. The ultrasound imaging probe of claim 1, further comprising a retention clip positioned around proximal ends of the plurality of heat spreader members.

3. The ultrasound imaging probe of claim 1, wherein the housing comprises a nosepiece sized and shaped to receive the ultrasound transducer assembly.

4. The ultrasound imaging probe of claim 1,
    wherein the plurality of fasteners comprise a plurality of shoulder screws.

5. The ultrasound imaging probe of claim 1, wherein the ultrasound transducer assembly comprises:
    a lens;
    a transducer array; and
    a backing block distinct from the chassis.

6. The ultrasound imaging probe of claim 1, further comprising a plurality of printed circuit boards coupled to the chassis, wherein the plurality of printed circuit boards are in communication with the ultrasound transducer assembly.

7. The ultrasound imaging probe of claim 1, further comprising a cable strain relief movably coupled to the plurality of heat spreader members, wherein in the uncured state the filling material is configured to allow movement of the cable strain relief relative to the plurality of heat spreader members.

8. The ultrasound imaging probe of claim 7, further comprising an elastic ring member,
    wherein the cable strain relief comprises a distal lip adjacent a distal end of the cable strain relief and a proximal lip proximal to the distal lip,
    wherein the distal lip of the cable strain relief is sized and shaped to engage a shoulder defined at proximal portions of the plurality of heat spreader members, and
    wherein when the distal lip engages the shoulder, the elastic ring member is disposed between the proximal lip and proximal ends of the plurality of heat spreader members.

9. The ultrasound imaging probe of claim 8, wherein the elastic ring member is formed of a thermally conductive elastomer.

10. The ultrasound imaging probe of claim 1, further comprising a thermally-conductive gap pad disposed between the chassis and at least one of the plurality of heat spreader members.

11. The ultrasound imaging probe of claim 1,
    wherein the plurality of fasteners comprises a plurality of screws, and
    wherein the first shape comprises a threaded portion and the second shape comprises an unthreaded portion.

12. The ultrasound imaging probe of claim 11,
    wherein each of the plurality of screws comprises a screw head,
    wherein the unthreaded portion is positioned between the screw head and the threaded portion such that an extent of the movement of the respective heat spreader member relative to the chassis is limited.

13. The ultrasound imaging probe of claim 1, wherein the filling material is formed of a room-temperature-vulcanizing rubber.

14. The ultrasound imaging probe of claim 1, wherein in the uncured state the filling material and the second portion of each of the plurality of fasteners are configured to allow movement of the plurality of heat spreader members in more than one dimension.

15. A method of manufacturing an ultrasound imaging probe, comprising:
    obtaining an ultrasound transducer assembly fixedly secured to a chassis;
    obtaining a plurality of heat spreader members;
    coupling the chassis to the plurality of heat spreader members using a plurality of fasteners, wherein each of the plurality of fasteners comprises:
        a first portion comprising a first shape fixedly secured to the chassis; and a second portion opposite to the first portion and interfacing with a respective heat spreader member, wherein the second portion comprises a different, second shape;

enclosing the plurality of heat spreader members, the chassis and the ultrasound transducer assembly in a housing, wherein the housing defines an interior space;

introducing a filling material in an uncured state into the interior space;

moving, with the filling material in the uncured state in the interior space, the plurality of heat spreader members within the interior space such that a positioning of the plurality of heat spreader members within the interior space adapts to dimensions of the interior space; and transitioning the filling material in the interior space from the uncured state into a cured state, wherein the plurality of heat spreader members is prevented from moving within the interior space when the filling material is in the cured state.

16. The method of claim 15, wherein the plurality of fasteners comprises a plurality of shoulder screws.

17. The method of claim 16, wherein the moving the plurality of heat spreader members comprises moving the plurality of heat spreader members about the plurality of shoulder screws in more than one dimension.

18. The method of claim 15, further comprising:
movably coupling a cable strain relief to proximal ends of the plurality of heat spreader members.

19. The method of claim 18, further comprising:
moving the plurality of heat spreader members relative to the cable strain relief.

20. The method of claim 18, wherein the movably coupling the cable strain relief to the proximal ends of the plurality of heat spreader members comprises coupling the cable strain relief to the proximal ends of the plurality of heat spreader members with an elastic ring member.

21. The method of claim 15, wherein the method further comprises:
coupling a thermally-conductive gap pad to at least one of the chassis or a heat spreader member of the plurality of heat spreader members, such that the thermally-conductive gap pad is positioned between the chassis and the heat spreader member.

* * * * *